US008333723B2

(12) United States Patent
Hunter et al.

(10) Patent No.: US 8,333,723 B2
(45) Date of Patent: Dec. 18, 2012

(54) KNEE BRACE WITH EXPANDABLE MEMBERS AND METHOD OF USING THE SAME

(75) Inventors: David J. Hunter, Vaucluse (AU); Glenn Colaco, Caringbah (AU); Dimitrije Stamenovic, Brookline, MA (US)

(73) Assignee: Trustees of Boston University, Boston, MA (US)

( * ) Notice: Subject to any disclaimer, the term of this patent is extended or adjusted under 35 U.S.C. 154(b) by 49 days.

(21) Appl. No.: 12/668,673

(22) PCT Filed: Jul. 18, 2008

(86) PCT No.: PCT/US2008/070494
§ 371 (c)(1),
(2), (4) Date: Jun. 3, 2010

(87) PCT Pub. No.: WO2009/012458
PCT Pub. Date: Jan. 22, 2009

(65) Prior Publication Data
US 2010/0241041 A1     Sep. 23, 2010

Related U.S. Application Data

(60) Provisional application No. 60/950,713, filed on Jul. 19, 2007.

(51) Int. Cl.
*A61F 5/00*     (2006.01)
(52) U.S. Cl. .............. 602/13; 602/16; 602/23; 602/26
(58) Field of Classification Search ............ 602/13, 602/16, 23–27; 128/882, DIG. 20; 2/22, 2/24
See application file for complete search history.

(56) References Cited

U.S. PATENT DOCUMENTS

| 3,581,741 | A |   | 6/1971 | Rosman et al. ................. 128/80 |
| 4,805,606 | A |   | 2/1989 | McDavid, III .............. 128/80 C |
| 4,953,543 | A | * | 9/1990 | Grim et al. ...................... 602/16 |
| 5,002,045 | A |   | 3/1991 | Spademan .................. 128/80 C |
| 5,360,394 | A | * | 11/1994 | Christensen .................... 602/26 |
| 5,415,625 | A | * | 5/1995 | Cassford et al. ............... 602/26 |
| 5,458,565 | A |   | 10/1995 | Tillinghast, III et al. ....... 602/26 |
| 5,545,911 | A | * | 8/1996 | Otsuki et al. .................. 257/376 |
| 5,797,864 | A |   | 8/1998 | Taylor ............................. 602/26 |
| 5,823,981 | A | * | 10/1998 | Grim et al. ...................... 602/26 |
| 5,865,166 | A |   | 2/1999 | Fitzpatrick et al. ........ 128/117.1 |

(Continued)

FOREIGN PATENT DOCUMENTS
WO     WO 01/45600     6/2001

OTHER PUBLICATIONS

Abbate et al., "Anthropometric Measures, Body Composition, Body Fat Distribution, and Knee Osteoarthritis in Women," *Obesity*, vol. 14, No. 7, pp. 1274-1281 (2006).

(Continued)

*Primary Examiner* — Michael A. Brown
(74) *Attorney, Agent, or Firm* — Sunstein Kann Murphy & Timbers LLP

(57) ABSTRACT

A knee brace (300) has a body (310) supporting first, second, and third expandable members (330). When expanded, the first, second, and third expandable members are positioned on the brace body to provide a counteracting force to the adduction moment of the knee.

45 Claims, 7 Drawing Sheets

Lateral-anterior view     Medial-anterior view
(y-axis is oriented toward central line of a body)

U.S. PATENT DOCUMENTS

| | | | |
|---|---|---|---|
| 6,110,138 A | 8/2000 | Shirley | 602/26 |
| 6,238,360 B1 | 5/2001 | Gildersleeve et al. | 602/26 |
| 6,336,909 B2 | 1/2002 | Gildersleeve et al. | 602/26 |
| 6,592,538 B1 | 7/2003 | Hotchkiss et al. | 602/26 |
| 6,994,682 B2 * | 2/2006 | Bauerfeind et al. | 602/26 |
| 7,083,586 B2 | 8/2006 | Simmons et al. | 602/23 |
| 7,198,610 B2 | 4/2007 | Ingimundarson et al. | 602/26 |
| 2002/0077574 A1 | 6/2002 | Gildersleeve et al. | 602/16 |
| 2006/0135900 A1 | 6/2006 | Ingimundarson et al. | 602/26 |
| 2006/0135901 A1 | 6/2006 | Ingimundarson et al. | 602/26 |
| 2006/0135902 A1 | 6/2006 | Ingimundarson et al. | 602/26 |
| 2006/0135904 A1 | 6/2006 | Ingimundarson et al. | 602/26 |
| 2006/0264793 A1 | 11/2006 | Simmons et al. | 602/23 |

OTHER PUBLICATIONS

Andriacchi, "Dynamics of Knee Malalignment," *Orthopedic Clinics of North America*, vol. 25, No. 3, pp. 395-403 (1994).

Basford et al., "Form May Be as Important as Function in Orthotic Acceptance: A Case Report," *Arch. Phys. Med. Rehabil.*, vol. 83, No. 3, pp. 433-435 (2002).

Cerejo et al., "The Influence of Alignment on Risk of Knee Osteoarthritis Progression According to Baseline Stage of Disease," *Arthritis & Rheumatism*, vol. 46, No. 10, pp. 2632-2636 (2002).

Ding et al., "A longitudinal study of the effect of sex and age on rate of change in knee cartilage volume in adults," *Rheumatology*; vol. 46, No. 2, pp. 273-279 (2007).

Felson et al., "Osteoarthritis: New Insights. Part 1: The Disease and Its Risk Factors", *Annals of Internal Medicine*, vol. 133, No. 8, pp. 635-646 (2000).

Felson et al., "Osteoarthritis: New Insights. Part 2: Treatment Approaches," *Annals of Internal Medicine*, vol. 133, No. 9 pp. 726-737 (2000).

Felson et al., "Bone Marrow Edema and Its Relation to Progression of Knee Osteoarthritis," *Annals of Internal Medicine*, vol. 139, No. 5 (Part 1), pp. 330-337 (2003).

Fredriks et al., "Nationwide age references for sitting height, leg length, and sitting height/height ratio, and their diagnostic value for disproportionate growth disorders," *Archives of Disease in Childhood*, vol. 90, No. 8, pp. 807-812 (2005).

Giori, "Load-shifting brace treatment for osteoarthritis of the knee: A minimum 2 ½-year follow-up study," *J. Rehabil. Res. Dev.*, vol. 41, No. 2, pp. 187-194 (2004).

Horlick et al., "Valgus Knee Bracing for Medial Gonarthrosis," *Clin. Journal of Sport Med.*, vol. 3, pp. 251-255 (1993).

Hunter et al., "Trapeziometacarpal subluxation predisposes to incident trapeziometacarpal osteoarthritis (OA): the Framingham Study," *Osteoarthritis & Cartilage*, vol. 13, No. 11, pp. 953-957 (2005).

Hunter et al., "The Association of Meniscal Pathologic Changes With Cartilage Loss in Symptomatic Knee Osteoarthritis," *Arthritis & Rheumatism*, vol. 54, No. 3, pp. 795-801 (2006).

Hurwitz et al., "The knee adduction moment during gait in subjects with knee osteoarthritis is more closely correlated with static alignment than radiographic disease severity, toe out angle and pain," *Journal of Orthopaedic Research*, vol. 20, No. 1, pp. 101-107 (2002).

Jordan et al., "EULAR Recommendations 2003: an evidence based approach to the management of knee osteoarthritis: Report of a Task Force of the Standing Committee for International Clinical Studies Including Therapeutic Trials (ESCISIT)," *Ann. Rheum. Dis.*, vol. 62, No. 12, pp. 1145-1155 (2003).

Kirkley et al., "The Effect of Bracing on Varus Gonarthrosis," *Journal of Bone and Joint Surgery*, vol. 81, No. 4, pp. 539-548 (1999).

Komistek et al., "An in vivo analysis of the effectiveness of the osteoarthritic knee brace during heel-strike of gait," *Journal of Arthroplasty*, vol. 14, No. 6, pp. 738-742 (1999).

Kraus et al., "A Comparative Assessment of Alignment Angle of the Knee by Radiographic and Physical Examination Methods," *Arthritis & Rheumatism*, vol. 52, No. 6, pp. 1730-1735 (2005).

Lawrence et al., "Estimates of the prevalence of arthritis and selected musculoskeletal disorders in the United States," *Arthritis & Rheumatism*, vol. 41, No. 5, pp. 778-799 (1998).

Lindenfeld et al., "Joint Loading With Valgus Bracing in Patients With Varus Gonarthrosis," *Clinical Orthopaedics & Related Research*, vol. 344, pp. 290-297 (1997).

Miyazaki et al., "Dynamic load at baseline can predict radiographic disease progression in medial compartment knee osteoarthritis," *Ann. Rheum. Dis.*, vol. 61, No. 7, pp. 617-622 (2002).

Morbidity & Mortality Weekly Report, "Arthritis Prevalence and Activity Limitations—United States," *MMWR*, vol. 43, No. 24, pp. 433-438 (1994).

Morbidity & Mortality Weekly Report, "Prevalence and Impact of Chronic Joint Symptoms—Seven States," *MMWR*, vol. 47, No. 17, pp. 345-351 (1998).

Najibi et al., "The use of knee braces, part 1: Prophylactic knee braces in contact sports," *American Journal of Sports Medicine*, vol. 33, No. 4, pp. 602-611 (2005).

Pollo et al., "Reduction of Medial Compartment Loads With Valgus Bracing of the Osteoarthritic Knee," *American Journal of Sports Medicine*, vol. 30, No. 3, pp. 414-421 (2002).

Sharma et al., "The Role of Knee Alignment in Disease Progression and Functional Decline in Knee Osteoarthritis," *JAMA*, vol. 286, No. 2, pp. 188-195 (2001).

Schipplein et al., "Interaction between active and passive knee stabilizers during level walking," *Journal of Orthopaedic Research*, vol. 9, No. 1, pp. 113-119 (1991).

Tetsworth et al., "Malalignment and degenerative arthropathy," *Orthopedic Clinics of North America*, vol. 25, No. 3, pp. 367-377 (1994).

Todd et al., "Naproxen. A reappraisal of its pharmacology, and therapeutic use in rheumatic diseases and pain states," *Drugs*, vol. 40, No. 1, pp. 91-137 (1990).

Wada et al., "Relationships among bone mineral densities, static alignment and dynamic load in patients with medial compartment knee osteoarthritis," *Rheumatology*; vol. 40, No. 5, pp. 499-505 (2001).

European Patent Officer Andreas Lickel, Authorized Officer, *International Search Report*—International Application No. PCT/US2008/070494, dated Oct. 7, 2008 (5 pages).

The International Bureau of WIPO Philippe Becamel, Authorized Officer, *International Preliminary Report on Patentability (with Written Opinion of the International Searching Authority)*—International Application No. PCT/US2008/070494, dated Jan. 19, 2010 (10 pages).

* cited by examiner

Lateral-anterior view                Medial-anterior view (y-axis is oriented toward central line of a body)

KNEE BRACE WITH EXPANDABLE MEMBERS AND METHOD OF USING THE SAME

PRIORITY

This patent application claims priority from U.S. provisional patent application Ser. No. 60/950,713, filed Jul. 19, 2007, and entitled "Knee Brace with Expandable Members and Method of Using the Same", the disclosure of which is incorporated herein, in its entirety, by reference.

FIELD OF THE INVENTION

The invention generally relates to knee braces and, more particularly, the invention relates to knee braces constructed to provide a counteracting force to the adduction moment or abduction moment of the knee.

BACKGROUND OF THE INVENTION

Affecting an estimated thirty percent of adults over age 55, knee osteoarthritis is one of the most frequent causes of lower limb disabilities. Unfortunately, the incidence of knee osteoarthritis in the United States, Europe, and other regions is expected to rise as populations age.

Safe and effective treatments of this disease are limited. For example, a number of current therapeutic modalities focus primarily on reducing pain and improving joint function by means of non-specific, symptomatic agents, such as non-steroidal anti-inflammatory drugs (NSAIDs) and COX-2 inhibitors. Undesirably, such agents are associated with high rates of adverse events. Moreover, these drugs rarely completely relieve symptoms. Many individuals with knee osteoarthritis thus ultimately require a total knee replacement.

The symptoms of knee osteoarthritis often are described as mechanical—they occur with activity. Despite the above noted shortcomings of drug therapy, attempts to ameliorate the forces in the knee with braces have proven effective in relieving symptoms. Clinically effective prior art braces, however, often are too bulky to comfortably wear for long periods, and difficult to wear underneath clothing.

SUMMARY OF THE INVENTION

In accordance with one embodiment of the invention, a knee brace has a body supporting first, second, and third expandable members. When expanded, the first, second, and third expandable members are positioned on the brace body to provide a counteracting force to the adduction moment of the knee.

When in use, the first and third expandable members illustratively are positioned to engage the interior part of the leg above and below the knee, while the second expandable member illustratively is positioned to engage the lateral part of the knee. Moreover, the brace also may have a hinge coupled with the second expandable member. Among other things, the hinge may have a stationary portion contacting the second expandable member, and a pivoting portion having a gel material that contacts the knee (when in use).

In illustrative embodiments, the body has a main portion formed of a flexible material (e.g., neoprene) and at least one nylon strap supporting one of the expandable members. Moreover, the first, second, and third expandable members each may include an inflatable bladder. The expandable members also may be fluidly connected and have a valve for controlling fluid flow (e.g., air) to each of them.

In accordance with another embodiment of the invention, a method of stabilizing a knee first provides a knee brace having a body supporting first, second, and third expandable members, and then positions the knee brace about the knee. Specifically, when positioned, the first and third expandable members are positioned on the interior portion of the leg above and below the knee, while the second expandable member is positioned on or very near to the lateral portion of the knee. The first, second, and third expandable members cooperate in this manner to provide a counteracting force to the adduction moment of the knee when expanded.

In accordance with additional embodiments of the present invention, a knee brace may also include a strap portion secured to a main portion. The main portion may be positionable over a subject's knee. The strap portion may have a plurality of expandable members (e.g., a first, second, and third expandable member) that provide a counteracting force to an adduction moment of the knee. For example, the expandable members may be inflatable bladders and provide the counteracting force when expanded.

The counteracting force may include three individual forces applied to the knee. For example, the first expandable member may apply a first force to the interior part of the leg above the knee. The second expandable member may apply a second force to the exterior part of the leg at the knee. Lastly, the third expandable member may apply a third force to the interior part of the leg below the knee.

In accordance with still further embodiments, the knee brace may also include a hinge member located on the strap member. The hinge member allows subject to bend the knee and may be coupled with the second expandable member. The hinge member may include a stationary portion that contacts the second expandable member and a pivoting portion that pivots within the stationary portion. The pivoting portion may also include a gel material that contacts the knee when in use.

In accordance with additional embodiments of the present invention, a knee brace may include a body portion, a first expandable member, a second expandable member, and a third expandable member. Each of the expandable members may be positioned on the body portion to provide a force on the knee. For example, the first expandable member may apply a first force to the medial part of the leg above the knee, the second expandable member may provide a second force to the lateral part of the leg at the knee, and the third expandable member may provide a third force to the medial part of the leg below the knee. The first, second, and third forces may combine to counteract an adduction moment of the knee.

In accordance with further embodiments, the knee brace may also include a strap member secured to the body portion. The strap member may support and mechanically connect the first, second, and third expandable members. The strap member may also have a non-elastic outer layer that prevents the first, second, and third expandable members from ballooning outwards.

In accordance with another embodiment of the present invention, a method for counteracting an adduction moment in the a knee can include positioning a knee brace over a knee having an adduction moment, and inflating a first, second, and third expandable members on the knee brace. In addition to the expandable members, the knee brace may also have a body portion. The inflated first, second, and third expandable members may each provide a force that, together, counteract the adduction moment of the knee. The expandable members may be inflated to a pressure that is dependent upon the user's level of activity.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a knee brace has a plurality of expandable members selectively positioned to provide a counteracting force to the adduction moment of a malaligned knee. To that end, the knee brace has a body supporting first, second, and third expandable members that apply force to the leg in a manner that counteracts the adduction moment. Details of illustrative embodiments are discussed below.

Figure 1A:
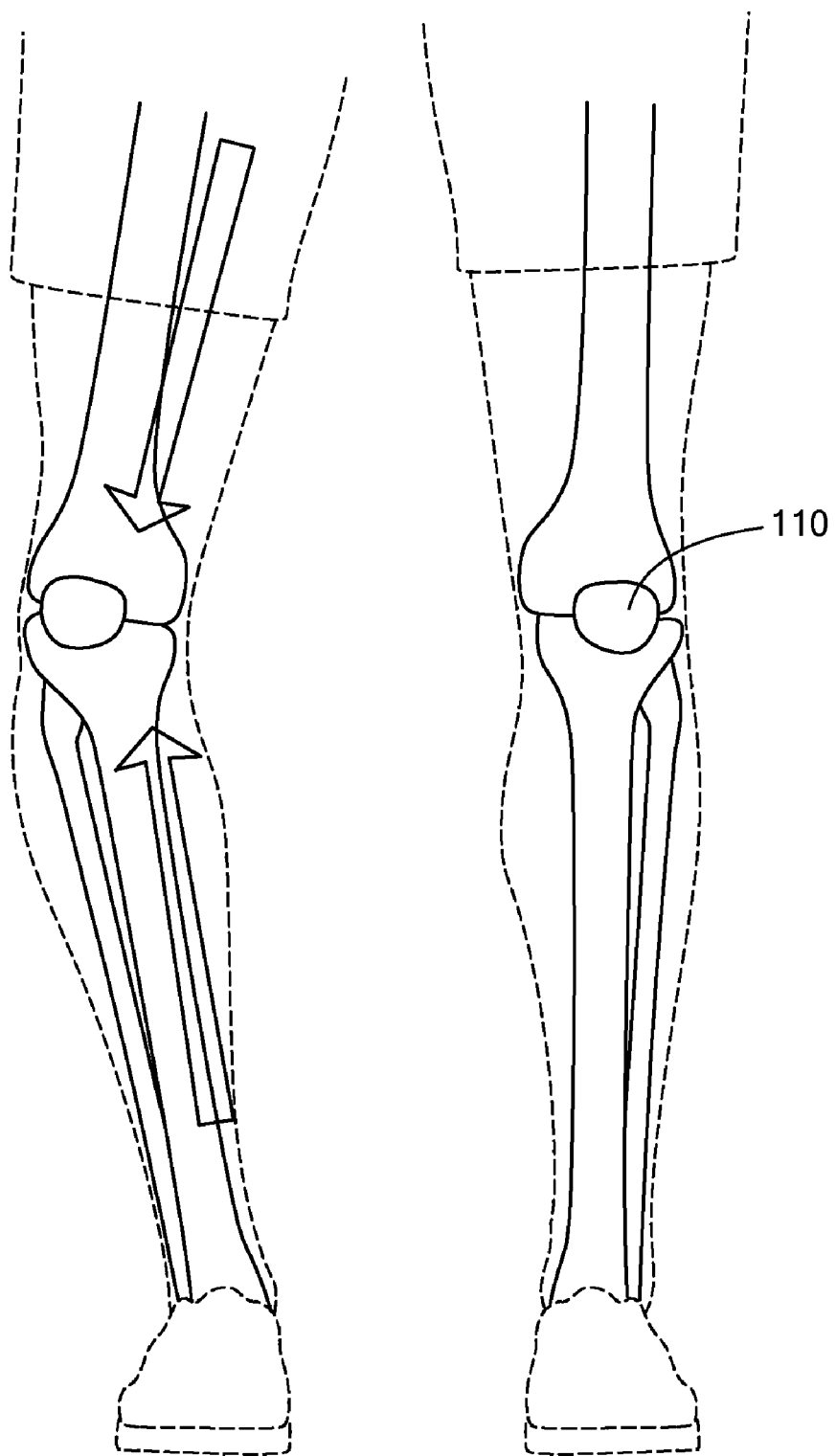
FIG. 1A schematically shows a human leg with malaligned knee that can be treated in accordance with illustrative embodiments of the invention.
Figure 1B:
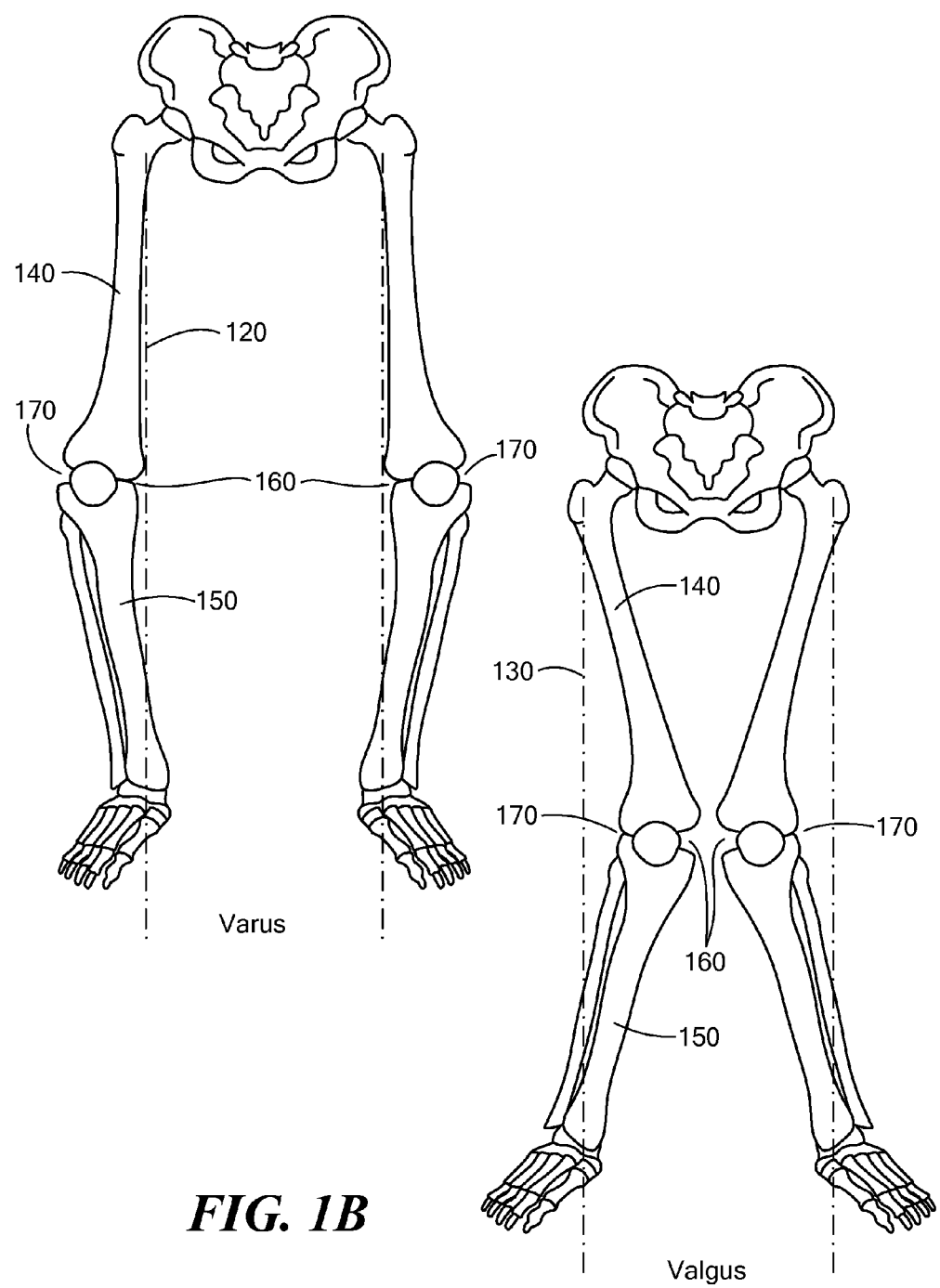
FIG. 1B schematically shows the skeletal structure of a human leg with a varus malaligned knee and the skeletal structure of a leg with a valgus malaligned knee.

FIGS. 1A and 1B schematically show human legs with malaligned knees that can be treated in accordance with illustrative embodiments of the invention. As shown in FIG. 1A, the leg on the left (i.e., the person's right leg) has a significant adduction moment, while the other leg appears approximately normal/neutral. Specifically, any shift from neutral or collinear alignment of the hip, knee, and ankle affects load distribution at the knee. The load-bearing axis is represented by a line drawn from the center of the femoral head to the center of the ankle. In a varus deformed knee (i.e., as shown in FIG. 1B), this line 120 passes medial to the knee center 110 to create an adduction moment arm, which increases the force across the medial compartment 160. In a valgus deformed knee, which is opposite to a varus deformed knee, the load-bearing axis 130 passes lateral to the knee center 110, and the resulting abduction moment arm increases the force across the lateral compartment 170.

Perhaps one of the clearest ways to visualize the impact of the adduction and abduction moments is in relation to the spacing of the knee. In a typical, healthy knee, the spacing between the femur 140 and the tibia 150 within the knee is primarily uniform. In other words, the space/gap between the femur 140 and tibia 150 are substantially the same within the medial compartment 160 and the lateral compartment 170. However, when the knee is malaligned (e.g., varus or valgus malalignment), the spacing may change and alter the load within the knee.

As shown in FIGS. 1B, when the knee suffers from a varus malalignment, the adduction moment reduces the space/gap between the femur 140 and the tibia 150 within the medial compartment 160 and increases the spacing/gap within the lateral compartment 170. Conversely, in a valgus malaligned knee, the abduction moment decreases the space/gap within the lateral compartment 170 and increases the space/gap within the medial compartment 160. The space/gap reduction in the respective compartments (e.g., the medial compartment 160 in the varus knee and the lateral compartment 170 in the valgus knee) increases the load and forces within the compartments. The increased load and forces, in turn, cause the symptoms described above (e.g., pain, loss of mobility, increased wear on the bones and cartilage, etc.). As described herein, various embodiments of the present invention provide forces on the knee that counteract the adduction moment. Illustrative embodiments, thus, counteract the load/forces within the medial and lateral compartments and return the spacing to a substantially normal level (e.g., increase the spacing/gap in the medial compartment 160 and reduce the spacing in the lateral compartment 170) in a varus knee.

The normal range for alignment differs depending on the study. For example, in many studies, neutral (normal) alignment is 1 degree varus (range 0-2 degrees). With increasing osteoarthritis of the medial compartment, the knee becomes increasingly varus (mean 3 degrees). Among varus knees, the mean±SD severity of varus was 3.13±1.25 degrees (range 1.00-5.00 degrees), in K/L grade 0-1 knees, 3.04±1.95 degrees (range 1.00-8.00 degrees), in grade 2 knees, and 4.34±2.6 degrees (range 1.00-10.00 degrees), in grade 3 knees (P not significant for grade 0-1 versus grade 2 knees; P=0.03 for grade 2 versus grade 3 knees).

Malalignment provides only a static impression of the mechanical forces being imparted on the joint in one plane. To appropriately determine these forces in more than one plane often requires 3-dimensional kinematic analysis. During the stance phase of gait, the force acting at the foot during gait passes medial to the center of the knee joint. The perpendicular distance from the line of action of this force and the center of the knee joint is the lever arm of this force. This force combined with this lever arm produces a moment that adducts the knee joint. This moment can be substantial and provide a major contribution to the total loading across the knee joint, which is usually labeled the adduction (or external varus) moment at the knee. The mean maximum magnitude of the adduction moment (M) during normal gait is approximately 3.3 percent body weight (W) times height (h) and is greater than either of the moments tending to flex or extend the knee. Studies of patients with medial knee osteoarthritis show that they have, on average, a higher M (4.2 percent W×h) than those without osteoarthritis.

Accordingly, illustrative embodiments create a force distribution around the knee that counterbalances this difference in M (referred to as ΔM) between a knee with osteoarthritis and a normal knee, i.e., ΔM=0.9 percent W×h. One study, for example, demonstrated the peak knee adduction moment in persons with moderate to severe osteoarthritis was 5.3 percent W×h (range 0.4-8.4 percent) versus those with mild osteoarthritis 3.5 percent (1.1-7.4 percent), with a p-value for difference that was 0.06. In persons without osteoarthritis, Hurwitz population would suggest the peak knee adduction moment is 3 percent W×h. This translates to a higher maximum reaction force on the medial compartment by 25 percent over normal values in those with medial knee osteoarthritis.

Figure 2:
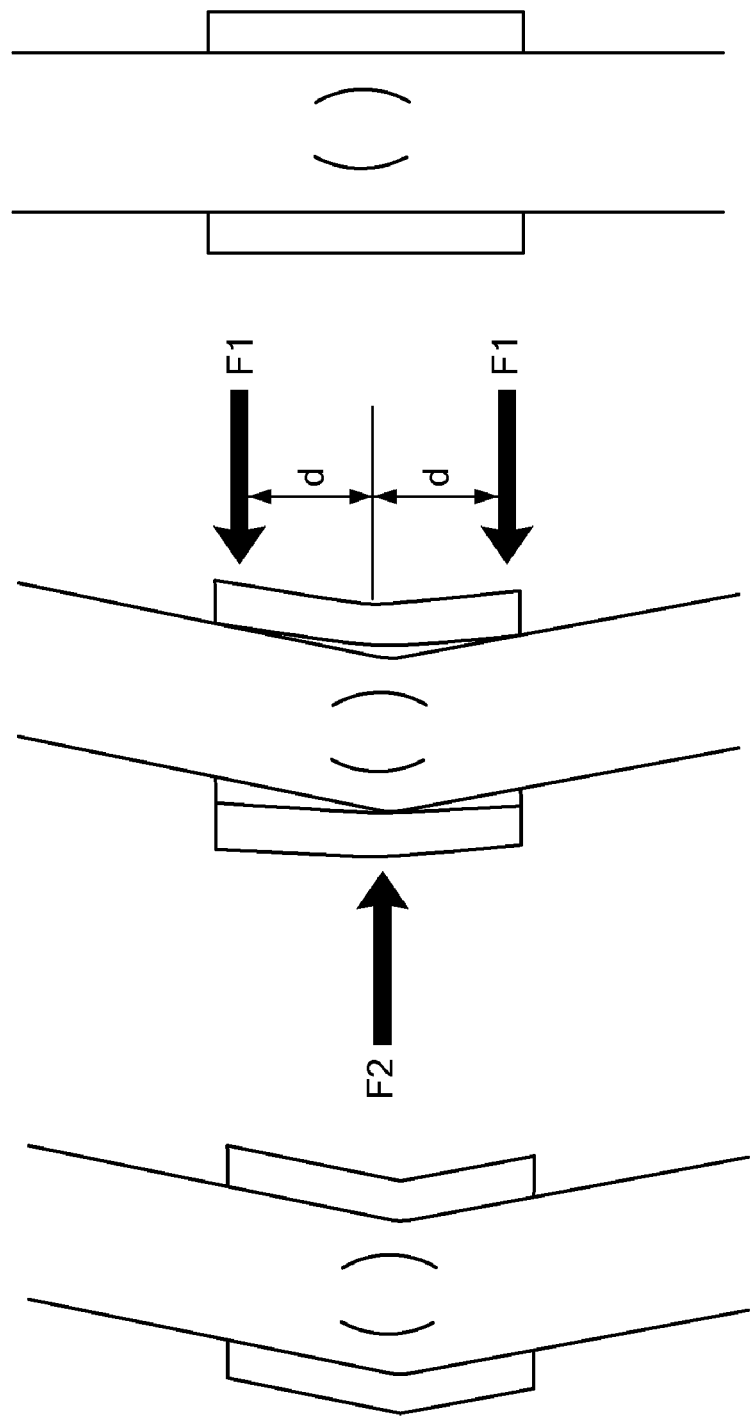
FIG. 2 schematically shows a generalized method of treating the malaligned knee shown in FIG. 1 by applying forces from inflatable members at the indicated sites.

Illustrative embodiments of the invention counterbalance the adduction moment by exerting forces on three strategic points along the leg. To that end, FIG. 2 schematically shows these forces, in which forces F1, which are exerted in an outward direction above and below the knee, substantially equal the force F2, which is exerted substantially at the knee and in an inward direction (i.e., in a direction that is opposite to the forces F1). For example, the forces F1 illustratively act an equal distance d from the point of application of the force F2. The moment produced by these forces that together counterbalance the abduction moment therefore equals the product of F1 and distance d. However, since illustrative embodiments of the knee brace are designed to counterbalance only the difference in that moment (also referred to as "delta M", which is equal to 0.9 percent W×h), it follows that:

$$F_1 = 0.9\% \; W \times h/d$$

Figure 3:
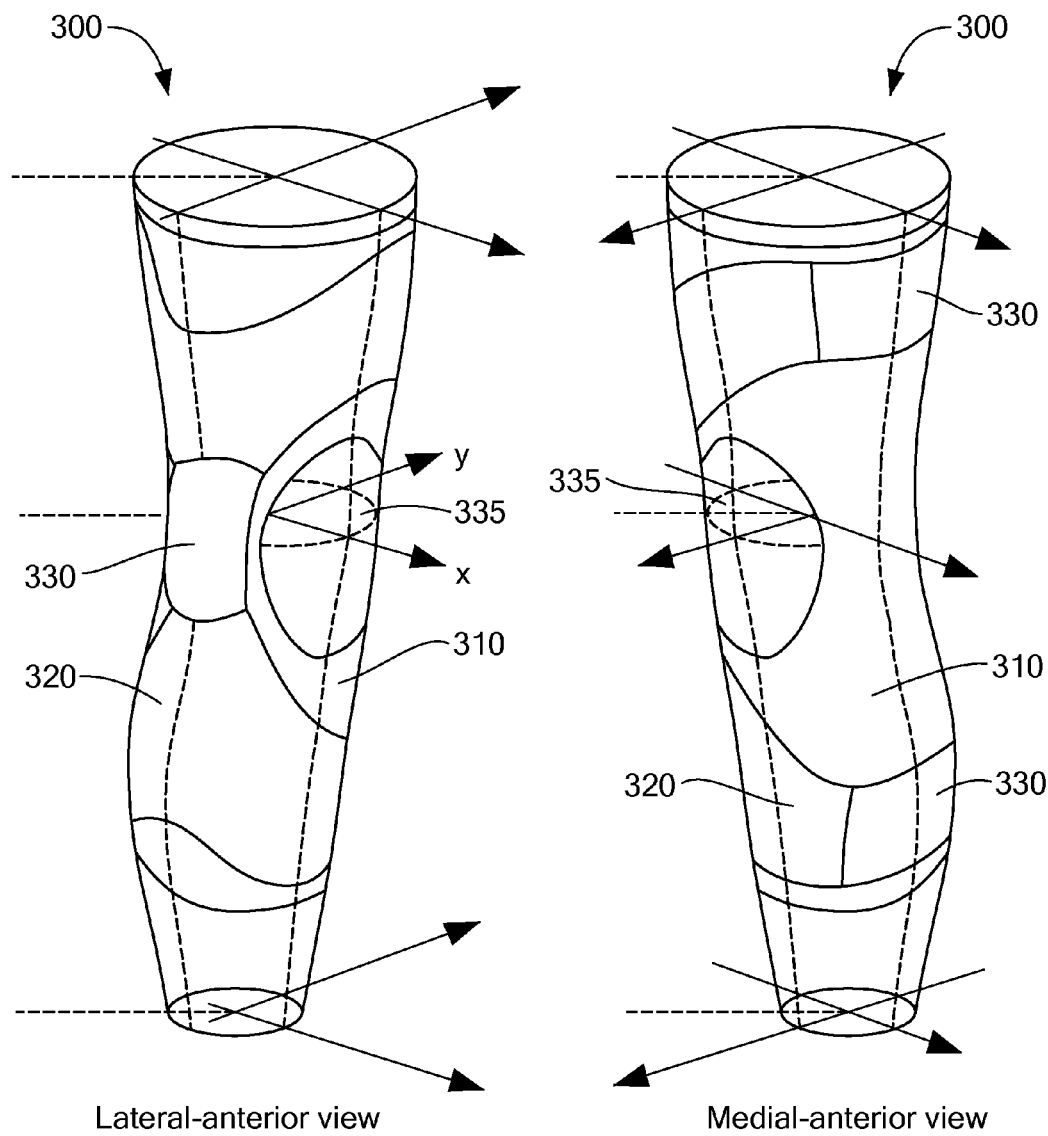
FIG. 3 schematically shows a knee brace produced in accordance with illustrative embodiments of the invention.
Figure 4:
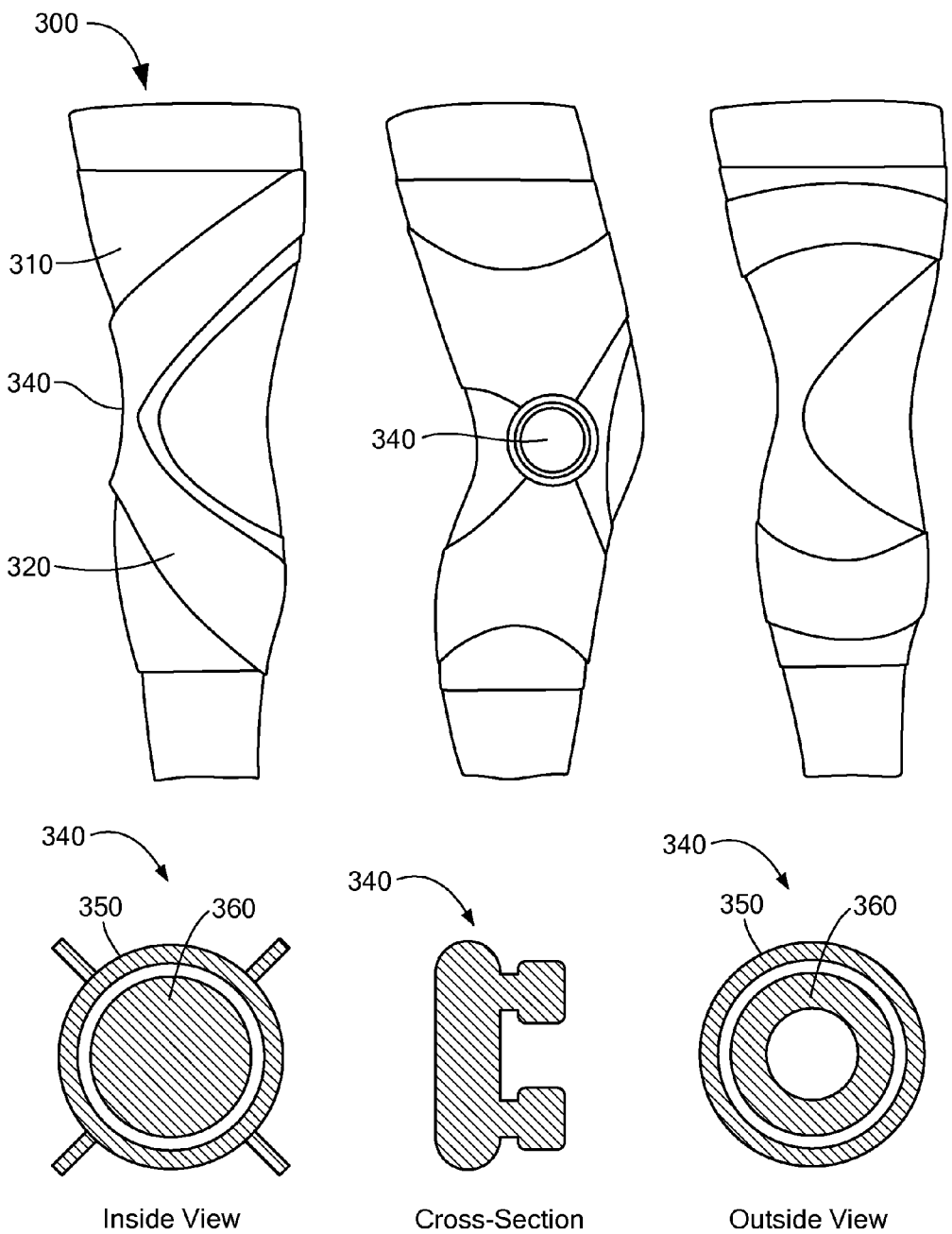
FIG. 4 schematically shows additional use of the knee brace shown in FIG. 3, including additional details of the hinge member.

To those ends, in accordance with illustrative embodiments, the forces F1 and F2 are applied by means of a system of expandable members 14, such as inflatable latex bladders 330 (also identified by reference number "14"), over prescribed contact areas to which the forces F1 and F2 point, respectively, in the figures. FIGS. 3 and 4 schematically show a right leg knee brace having such members.

Specifically, as shown in those figures, the knee brace 300 has a body 310 forming a plurality of straps 320 supporting the bladders 330 (only schematically shown), and a hinge 340 for facilitating movement. In illustrative embodiments, the portion of the body 310 having no bladders 330 is formed simply from a flexible material, such as neoprene. The knee brace 300 may also have an opening 335 located on the anterior part of the brace 300. When the brace 300 is in use, the opening 335 may be positioned over the knee cap to ensure proper positioning of the brace 300.

Figure 5A:
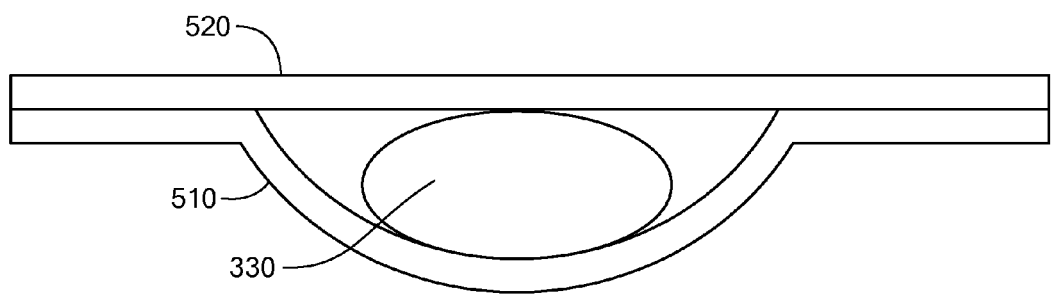
FIG. 5A schematically shows additional detail of the strap member and inflatable member, in accordance with illustrative embodiments of the present invention.

As shown in FIG. 5A, the portions of the body 310 having the bladders 330 producing force F1, however, have a more complex arrangement. In particular, those portions of the body 310 have a plurality of layers starting with an inner, relatively soft, pliable material layer 510 that removably adheres to the skin. For example, this inner layer 510 may be formed from neoprene. The next adjacent layer includes the inflatable bladder, which should fixedly adhere to neoprene. Among other things, the inflatable bladder 330 may take the form of a latex balloon. Finally, the knee brace 300 has an exterior, relatively non-elastic material layer 520 (e.g., nylon) that firmly resists outward expansion of the bladder. Consequently, rather than increasing the outer diameter of the brace 10, expansion of the bladder 330 at that point should substantially reduce the inner diameter of the brace 10.

The portion of the body 310 applying the inwardly directed force F2 has an even more complex arrangement than the other portions described above. Specifically, this portion is configured to permit the leg to freely pivot without compromising the structural integrity of the bladder. To that end, in addition to a soft pliable layer 510, inflatable bladder 330, and outer non-elastic layer 520, the knee brace 300 may also include the above noted hinge 340 that extends through the soft pliable layer 510 (e.g., the neoprene layer) and the non-elastic layer 520 (e.g., the nylon layer). Generally, the hinge 340 may have a movable portion and a fixed portion (relative to the knee) radially inward of the movable portion. The movable portion may be connected with the soft inner layer (or body portion 310), while the fixed portion may be connected with the next succeeding layer; namely, the inflatable bladder 330. The strap member 320 or non-elastic material may help resist outward expansion of the bladder 330.

Figure 5B:
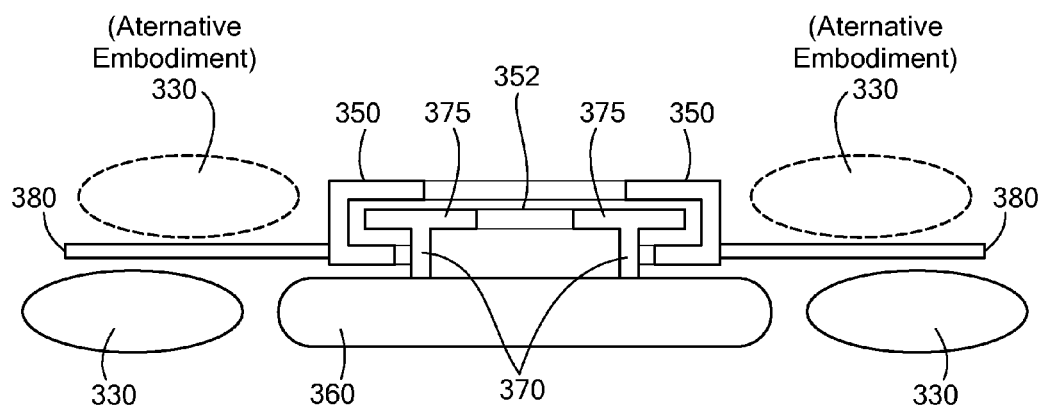
FIG. 5B schematically shows a cross-section and additional details of the hinge shown in FIG. 4, in accordance with embodiments of the present invention FIGS. 6A and 6B schematically show higher stress areas of the knee brace shown in FIGS. 2-4.

As shown in FIGS. 4 and 5B, the hinge 340 may include a condylar pad 360, protrusion 370, and coupling 350. The condylar pad 360 removeably adheres the lateral portion of the knee at the location of F2 and may be made from a soft silicon gel that has a consistency analogous to that of a baby teething ring. Although the condylar pad 360 may rotate with respect to the coupling 350, the condylar pad 360 should not rotate relative to the knee (e.g., it should maintain contact and move with the knee).

Protruding from the lateral side of the condylar pad 360, the hinge 340 has a protrusion 370 that engages with the coupling 350. The protrusion 370 can be any number of structures including, but not limited to, an annular ring or a series of post members. As mentioned above, the protrusion 370 engages with the coupling 350. To that end, the coupling 350 can have a track 355, in which the protrusion 370 may sit. To prevent disengagement, the protrusion 370 may have a thicker portion 375 towards the end of the protrusion 370. In such embodiments, the protrusion 370 may be "snapped" into the track 355 and the thicker portion 375 will prevent the protrusion 370 and, thus, the condylar pad 360 from disengaging from the coupling 350. Once assembled, the condylar pad 360 and protrusion 370 can move relative to the coupling 350.

To facilitate the application of force F1 and attachment with the inflatable bladder 330, the hinge 340 can have arm member(s) 380 that extend radially outward (e.g., above and below) from the hinge 340. As shown in FIG. 5B, the inflatable bladder 330 can be located below these arm member(s) 380. As the bladder 330 is inflated (e.g., to exert force F1 on the knee), the arm member(s) 380 prevent the bladders 330 from ballooning out and ensure that the force is applied to the knee.

As one may expect, the presence of the inflatable bladders 330 under the arm member(s) 380 may tend to lift the condylar pad 360 off the knee when the bladders 330 are inflated. However, in illustrative embodiments of the present invention, the body portion 310 and the strap members 320 prevent this from happening. In particular, because the body portion 310 and the strap members 320 are kept tight on the subject, the two components are able to keep the condylar pad 360 in contact with the knee at all times. Additionally, as mentioned above, the body portion 310 and the strap members 320 also help prevent the bladders 330 from ballooning out and help the knee brace 300 effectively apply the force F2 to the knee.

As shown in FIG. 5B, the coupling 350 can be an annular ring having an opening 352. The opening 352 provides the user with access to the inflatable bladder 330 (e.g., to inflate the bladder(s) 330). For example, the knee brace may have a tube (not shown) extending from the inflatable bladder(s) 330 to the opening 352. The user may then inflate the bladder(s) 330 in any of the manners described below (e.g., hand pump, electric pump, blowing into a one-way valve, etc.).

As mentioned above, the inflatable bladder 330 may be located below the arm member(s) 380. In alternative embodiments, the inflatable bladder(s) 330 may be located above the arm member(s) 380 (shown in dashed lines in FIG. 5B). In such embodiments, when inflated, the bladder(s) 380 will exert a force on the arm member(s) 380 that is directed towards the knee. The arm members 380 will, in turn, translate the force to the hinge 340 and condylar pad 360. In such embodiments, the hinge 340 and condylar pad 360 apply the force F2 to the lateral portion of the knee and there may be no direct contact between the inflatable bladder(s) 330 and the skin.

It is important to note that the number and style of bladder(s) 330 used at this location can vary. For example, some embodiments of the knee brace 300 may only have a single annular bladder 330 that surrounds the hinge 340. Alternatively, the knee brace 300 may have one or more arm member(s) 380 (e.g., as described above) and a single bladder 330 located above and/or below each of the arm member(s) 380. For example, if the hinge 340 has two arm members 380 (e.g., one extending up toward the subject's hip and one extending down towards the subject's foot), the knee brace 300 can have an inflatable bladder 330 located above and/or below each of the two arm members 380. Alternatively, the hinge 340 can have four arm members 380 extending radially out from the center of the hinge 340 and the knee brace 300 can have a bladder 330 located above and/or below each of the four arm members 380. Although illustrative embodiments of the hinge 340 are described above, it is important to note that other hinge mechanisms and orientations may be used and thus, the examples mentioned above are simply for discussion purposes only.

Although the body 310 is described above as forming a plurality of straps 320 for supporting the bladders, other embodiments may have different configurations. For example, the knee brace may have separate body portions 310 and strap members 320 (e.g., the body 310 does not form the straps) that may or may not be secured to the body portion 310. In such embodiments, the body portion 310 may be made from an elastic material, such as neoprene. This allows the knee brace to easily slide over and conform to the subject's knee and leg. Conversely, the strap members 320 may be made from a less elastic material, for example, nylon reinforced neoprene (e.g., neoprene with an outer layer of non-elastic nylon to prevent the bladders from ballooning out). The non-elastic nature of the outer layer 520 also allows the strap members 320 to mechanically connect the bladders 330.

In a manner similar to that described above, the strap members 320 may support the inflatable bladders 330. For example, as shown in FIG. 5A, the flexible layer 510 (e.g., the neoprene) may be located on the inner portion of the strap member 320 and may contact the knee or the body portion 310 of the brace 300. The non-elastic layer 520 (e.g., the nylon layer) may be located on the outside of the strap member 320. The inflatable bladder 330 may be located between the two layers. In this configuration, the soft flexible layer 510 contacts the subject (or body portion 310) and allows the inflatable bladder 330 to expand towards the knee and apply the forces described above. The non-elastic layer prevents the bladders 330 from ballooning out. Additionally, as described above, the strap member 320 may also include a layer or section of soft silicon gel (e.g., at the hinge 340) that contacts and removably adheres to the skin to provide additional comfort for the user.

In still further embodiments, the strap members 320 may just simply be a single layer of non-elastic material (e.g., similar to the outer nylon layer 520) described above. In such embodiments, the strap members 320, the body portion 310, and the bladders 330 combine to form the three layers described above. In particular, the body portion 310 acts as the inner elastic layer 510, the strap members 320 act as the outer non-elastic layer 520, and the bladders 330 may be located between them.

Although not shown, the knee brace 300 also has a channel for directing fluid flow into and out of the inflatable bladders 330. The force applied by the bladders 330 may be controlled by some additional means, such as a valve. Accordingly, a user may inflate the bladders 330 to any desired pressure as required by their condition. In other words, the knee brace 300 is customizable to apply an appropriate pressure (e.g., 7 psi) based upon the needs of the user. For example, a user engaging in vigorous exercise may inflate the bladders 330 more than a user taking a short walk. The user should be instructed, however, not to inflate the bladders 330 in a manner that would constrict blood flow. For example, it has been shown that pressures above 12 psi may cause discomfort and problems with blood flow.

Conventional inflation mechanisms may be used to inflate the expandable bladders 330. For example, a simple hand pump or more complex electric pump may provide the air pressure. Alternatively, the valve may be a simple one way valve that permits a user to manually blow into the bladders 330. Additionally or alternatively, the bladders 330 may be self-inflating. Of course, other inflation mechanisms may be used and thus, the examples mentioned above are simply for discussion purposes only. For example, a liquid may serve as the fluid within the bladders 330.

In use, prior to performing a given activity, the user may simply slide the knee brace over their knee. As mentioned above, the body 310 of the knee brace is made of flexible material such that the knee brace will slide over the user's knee/leg like a sock or sleeve. Once in position, the user may then inflate the bladders 330, which, when inflated, will provide the forces (e.g., the two F1 forces and the F2 force) to counteract the adduction moment within the knee. In some embodiments, the user may inflate the bladders 330 to different pressures depending on the user's level of activity. For example, if the user is going for a leisurely walk, the user may inflate the bladders 330 to a relatively low level/pressure. However, if the user is performing a more strenuous activity (e.g., running, biking, playing a sport, etc.) the user may inflate the bladders to a higher level/pressure to increase the forces applied to the knee.

In some embodiments, the portions of the body 310 having one or more bladders 330 effectively form straps 320. In other embodiments, the portions of the body 310 having the bladders 330 do not form straps 320, or some form straps 320 and others do not form straps 320. Moreover, some embodiments may have more than three bladders 330. For example, rather than use a single bladder 330, expandable members slightly above and below the knee may provide the force F2.

Figures 6A, 6B:
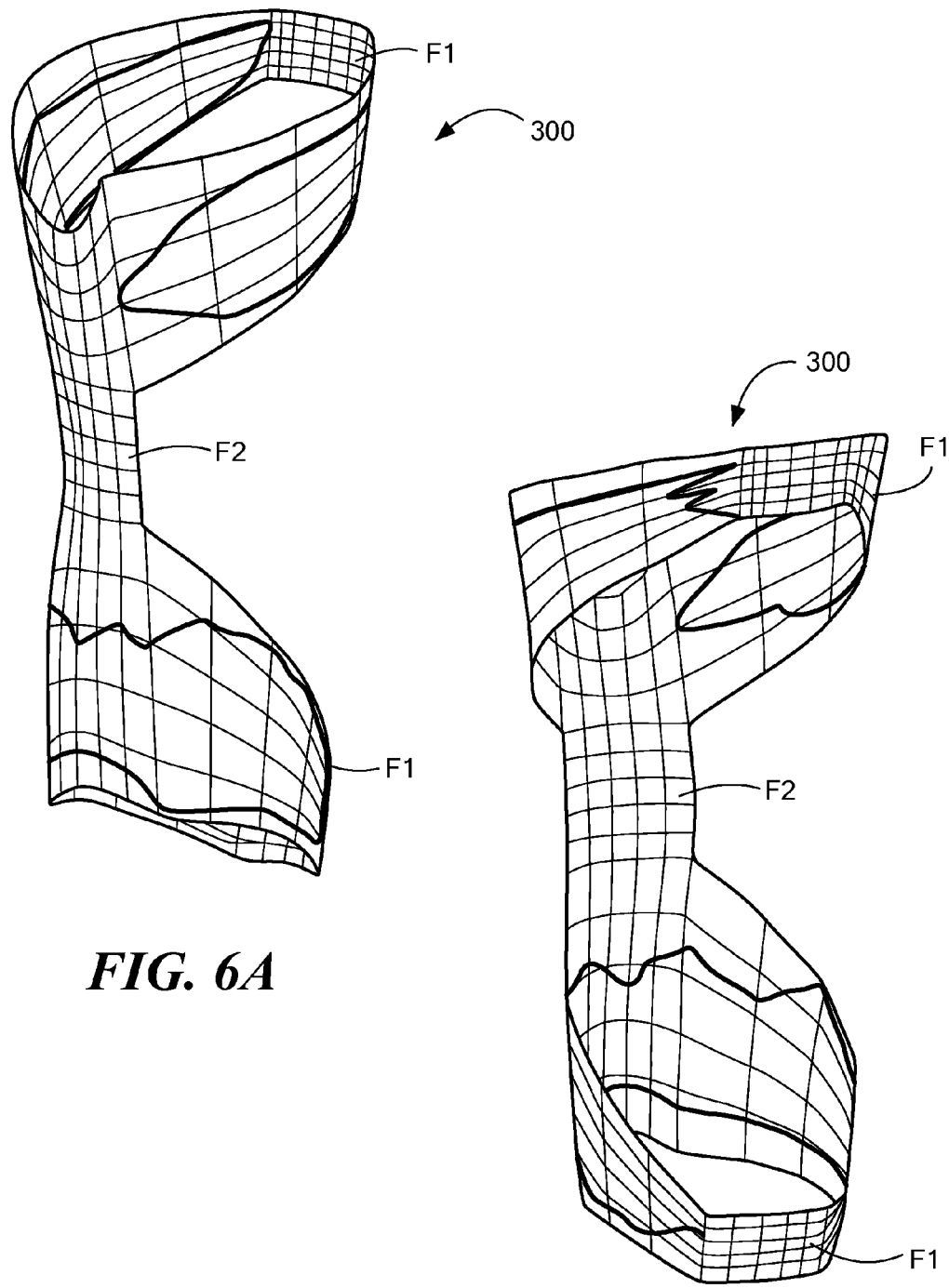

FIGS. 6A and 6B schematically shows the force points F1 and F2 of the brace 300 with much of the rest of the body 310 removed (for illustrative purposes). Some embodiments of the brace 300 may have only corresponding portions, while others have the rest of the body 310 (i.e., the part discussed above as having only a soft material).

It should be noted that discussion of specific materials and types of devices are not intended to limit various aspects of the invention. For example, devices other than latex bladders 330 may be used as expandable members, or the body 310 and/or strap members 320 may be formed from different materials having similar physical properties.

Illustrative embodiments of the knee brace 300 thus may be easily adjustable to the needs of a specific individual. Moreover, this knee brace 300 should be relatively easy to position on the leg. For example, as described above, the knee brace 300 may be simply slid over a person's leg in a manner similar to sliding a sock over a person's foot. In addition, the hinge design should enable the knee to move through its full range of motion without significant resistance. Finally, this knee brace 300 should be less bulky than conventionally effective designs, thus more readily permitting it to be worn under clothing.

Some alternative embodiments may be applicable to the opposite problem; namely, a valgus deformed knee. Accordingly, in such embodiments, the positioning of the bladders 330 may be reversed to provide the force F2 in an outward direction at the knee, and the forces F1 and an inward direction above and below the knee. In other words forces, in such embodiments, the knee brace will provide forces F1 on the lateral part of the leg, above and below the knee and force F2 on the medial part of the leg at the knee.

Although the above discussion discloses various exemplary embodiments of the invention, it should be apparent that those skilled in the art can make various modifications that will achieve some of the advantages of the invention without departing from the true scope of the invention.

What is claimed is:

1. A knee brace comprising:
   a body supporting first, second, and third expandable members,
   the first, second, and third expandable members being positioned on the body to provide a counteracting force to the adduction moment of the knee when the expandable members are expanded; and
   a hinge coupled with the second expandable member, the hinge including a stationary portion and a pivoting portion, the stationary portion contacting the second expandable member, the pivoting portion comprising a gel material that contacts the knee when in use.

2. The knee brace as defined by claim 1 wherein the first and third expandable members are positioned to engage the interior part of the leg above and below the knee when in use, the second expandable member being positioned to engage the lateral part of the knee when in use.

3. The knee brace as defined by claim 1 wherein the body comprises at least one strap supporting one of the expandable members and comprising nylon.

4. The knee brace as defined by claim 1 wherein the first, second, and third expandable members each comprise an inflatable bladder.

5. The knee brace as defined by claim 1 wherein the body comprises a plurality of straps and a main portion comprising neoprene.

6. The knee brace as defined by claim 1 wherein the first, second, and third expandable members are fluidly connected, the knee brace further comprising a valve for controlling fluid flow to the expandable members.

7. A method of stabilizing a knee, the method comprising:
   providing a knee brace having a body supporting first, second, and third expandable members; and
   positioning the knee brace about the knee, positioning causing the first and third expandable members to be positioned on the interior portion of the leg above and below the knee, positioning also causing the second expandable member to be positioned on the lateral portion of the knee, the first, second, and third expandable members cooperating to provide a counteracting force to the adduction moment of the knee when expanded, the knee brace including a hinge coupled with the second expandable member and including a stationary portion and a pivoting portion, the stationary portion contacting the second expandable member, the pivoting portion comprising a gel material that contacts the knee when in use.

8. A knee brace comprising:
   a main portion positionable over a subject's knee;
   a strap portion secured to the main portion and having a plurality of expandable members, the expandable members positioned to provide a counteracting force to an adduction moment of the knee; and
   a hinge member located on the strap member, the hinge member allowing the subject to bend the knee.

9. A knee brace according to claim 8, wherein the plurality of expandable members provides the counteracting force when expanded.

10. A knee brace according to claim 8, wherein the plurality of expandable members includes a first, second and third expandable member.

11. A knee brace according to claim 10, wherein the counteracting force includes a first force applied by the first expandable member to the interior part of the leg above the knee, a second force applied by the second expandable member to the exterior part of the leg at the knee, and a third force applied by the third expandable member to the interior part of the leg below the knee.

12. A knee brace according to claim 8, wherein the hinge member is coupled with the second expandable member.

13. A knee brace according to claim 8, wherein the hinge member comprises a stationary portion and a pivoting portion, the stationary portion contacting the second expandable member, the pivoting portion pivoting within the stationary portion.

14. A knee brace according to claim 13, the pivoting portion comprising a gel material that contacts the knee when in use.

15. A knee brace according to claim 8, wherein the plurality of expandable members each comprise an inflatable bladder.

16. A knee brace comprising:
   a body portion;
   a first expandable member positioned on the body portion to provide a first force, the first force applied to the medial part of the leg above the knee;
   a second expandable member positioned on the body portion to provide a second force, the second force applied to the lateral part of the leg at the knee;
   a third expandable member positioned on the body portion to provide a third force, the third force applied to the medial part of the leg below the knee; and
   a hinge member located on the body portion, the hinge member allowing the subject to bend the knee, the hinge member including a stationary portion and a pivoting portion, the stationary portion contacting the second expandable member, the pivoting portion pivoting within the stationary portion.

17. A knee brace according to claim 16, wherein the first, second, and third forces combine to counteract an adduction moment of the knee.

18. A knee brace according to claim 16, wherein the first, second, and third expandable members provide the first, second, and third force when expanded.

19. A knee brace according to claim 16, wherein the hinge member is coupled with the second expandable member.

20. A knee brace according to claim 16, the pivoting portion comprising a gel material that contacts the knee when in use.

21. A knee brace according to claim 16, wherein the plurality of expandable members each comprise an inflatable bladder.

22. A knee brace according to claim 16, further comprising a strap member secured to the body portion, the strap member supporting the first, second, and third expandable members.

23. A knee brace according to claim 22, wherein the strap member includes a non-elastic outer layer that prevents the first, second, and third expandable members from ballooning outwards.

24. A knee brace according to claim 23, wherein the strap member mechanically connects the first, second, and third expandable members.

25. A method of counteracting an adduction moment in a knee comprising:
positioning a knee brace over a knee having an adduction moment, the knee brace having a body portion and a first, second, and third expandable member;
inflating the first, second, and third expandable members, the inflated first, second, and third expandable members providing a first, second, and third force, the first, second, and third force counteracting the adduction moment of the knee, wherein inflating the first, second, and third expandable members includes inflating the first, second, and third expandable members to a pressure that is dependent upon a level of activity.

26. A method according to claim 25, wherein the knee brace further includes a hinge member located on the body portion and coupled with the second expandable member, the hinge member allowing the subject to bend the knee.

27. A method according to claim 26, wherein the hinge member comprises a stationary portion and a pivoting portion, the stationary portion contacting the second expandable member, the pivoting portion pivoting within the stationary portion.

28. A method according to claim 25, wherein the expandable members each comprise an inflatable bladder.

29. A method according to claim 25, wherein the knee brace further includes a strap member secured to the body portion, the strap member supporting the first, second, and third expandable members.

30. A knee brace comprising:
a body portion;
a first expanding means for providing a first force, the first expanding means positioned on the body portion, the first force applied to the medial part of the leg above the knee;
a second expanding means for providing a second force, the second expanding means positioned on the body portion, the second force applied to the lateral part of the leg at the knee;
a third expanding means for providing a third force, the third expanding means positioned on the body portion, the third force applied to the medial part of the leg below the knee; and
a strapping means for supporting the first, second, and third expanding means, the strapping means being secured to the body portion, wherein the strapping means includes a restraining means for preventing the first, second, and third expanding means from ballooning outwards.

31. A knee brace according to claim 30 further comprising a hinge means for allowing the subject to bend the knee.

32. A knee brace according to claim 30, wherein the strapping means also mechanically connects the first, second, and third expanding means.

33. A knee brace comprising:
a body portion;
a first expandable member positioned on the body portion to provide a first force, the first force applied to the medial part of the leg above the knee;
a second expandable member positioned on the body portion to provide a second force, the second force applied to the lateral part of the leg at the knee;
a third expandable member positioned on the body portion to provide a third force, the third force applied to the medial part of the leg below the knee; and
a strap member secured to the body portion, the strap member supporting the first, second, and third expandable members, and including a non-elastic outer layer that prevents the first, second, and third expandable members from ballooning outwards.

34. A knee brace according to claim 33, wherein the first, second, and third forces combine to counteract an adduction moment of the knee.

35. A knee brace according to claim 33, wherein the first, second, and third expandable members provide the first, second, and third force when expanded.

36. A knee brace according to claim 33 further comprising a hinge member located on the body portion, the hinge member allowing the subject to bend the knee.

37. A knee brace according to claim 36, wherein the hinge member is coupled with the second expandable member.

38. A knee brace according to claim 36, wherein the hinge member comprises a stationary portion and a pivoting portion, the stationary portion contacting the second expandable member, the pivoting portion pivoting within the stationary portion.

39. A knee brace according to claim 38, the pivoting portion comprising a gel material that contacts the knee when in use.

40. A knee brace according to claim 33, wherein the plurality of expandable members each comprise an inflatable bladder.

41. A knee brace according to claim 33, wherein the strap member mechanically connects the first, second, and third expandable members.

42. A method of counteracting an adduction moment in a knee comprising:
positioning a knee brace over a knee having an adduction moment, the knee brace having a body portion and a first, second, and third expandable member, the knee brace further including a hinge member located on the body portion and coupled with the second expandable member, the hinge member allowing the subject to bend the knee and including a stationary portion and a pivoting portion, the stationary portion contacting the second expandable member, the pivoting portion pivoting within the stationary portion;
inflating the first, second, and third expandable members, the inflated first, second, and third expandable members providing a first, second, and third force, the first, second, and third force counteracting the adduction moment of the knee.

43. A method according to claim 42, wherein inflating the first, second, and third expandable members includes inflating the first, second, and third expandable members to a pressure that is dependent upon a level of activity.

44. A method according to claim 42, wherein the expandable members each comprise an inflatable bladder.

45. A method according to claim 42, wherein the knee brace further includes strap member secured to the body portion, the strap member supporting the first, second, and third expandable members.

* * * * *